US005858378A

United States Patent [19]

Bostwick

[11] Patent Number: 5,858,378

[45] Date of Patent: Jan. 12, 1999

[54] **PHARMACEUTICAL COMPOSITION COMPRISING *CRYPTOSPORIDIUM* PARVUM OOCYSTS ANTIGEN AND WHOLE CELL CANDIDA SPECIES ANTIGEN**

[75] Inventor: Eileen F. Bostwick, Dayton, Minn.

[73] Assignee: Galagen, Inc., Arden Hills, Minn.

[21] Appl. No.: 643,032

[22] Filed: May 2, 1996

[51] Int. Cl.$^6$ .................... A61K 39/00

[52] U.S. Cl. .................... 424/274.1; 514/54; 536/117

[58] Field of Search .................... 424/274.1; 514/54; 536/117

[56] References Cited

U.S. PATENT DOCUMENTS

| | | | |
|---|---|---|---|
| 4,603,112 | 7/1986 | Paoletti et al. | 435/235.1 |
| 4,678,748 | 7/1987 | Sutker et al. | 435/71.1 |
| 4,739,046 | 4/1988 | DiLuzio | 536/117 |
| 4,761,402 | 8/1988 | Williams et al. | 514/54 |
| 4,877,612 | 10/1989 | Berger et al. | 424/282.1 |
| 4,877,777 | 10/1989 | Di Luzio | 514/54 |
| 4,971,956 | 11/1990 | Suzuki et al. | 514/55 |
| 5,057,503 | 10/1991 | Czop et al. | 424/278.1 |
| 5,106,616 | 4/1992 | McAnalley et al. | 424/85.2 |
| 5,106,618 | 4/1992 | Beck et al. | 424/57.1 |
| 5,217,898 | 6/1993 | Kaslow et al. | 435/254.2 |
| 5,288,639 | 2/1994 | Burnie et al. | 435/320.1 |
| 5,374,423 | 12/1994 | Klimpel et al. | 424/85.1 |
| 5,429,818 | 7/1995 | Inzana | 424/256.1 |
| 5,470,835 | 11/1995 | Kirkpatrick et al. | 514/21 |
| 5,531,988 | 7/1996 | Paul | 424/93.4 |
| 5,538,733 | 7/1996 | Emery et al. | 424/422 |
| 5,591,434 | 1/1997 | Jenkins | 424/191.1 |

FOREIGN PATENT DOCUMENTS

| | | |
|---|---|---|
| 929143 | 11/1992 | South Africa . |
| GB86/00142 | 9/1986 | WIPO . |
| 93/24649 | 9/1993 | WIPO . |
| SE93/00353 | 11/1993 | WIPO . |
| 93/24649 | 12/1993 | WIPO . |
| 9324649 | 12/1993 | WIPO . |

OTHER PUBLICATIONS

K. W. Angus, “Cryptosporidiosis and AIDS,” *Baillière's Clinical Gastroenterology*, 4:425–441 (Jun. 1990).

Barrios et al. Mycobacterial heat–shock proteins as carrier molecules. II: The use of the 70–kDa mycobacterial heat–shock protein as carrier for conjugated vaccines can circumvent the need for adjuvants and Bacillus Calmette Guerin priming, *Eur. J. Immunol.* 22: 1365–72 (1992).

Florence G. Crawford et al., “Human Cryptosporidiosis,” *CRC Critical Reviews in Microbiology*, 16:113–159 (1988).

Edward N. Janoff et al., “Cryptosporidium Species, a Protean Protozoan,” *Journal of Clinical Microbiology*, 25:967–975 (Jun. 1987).

Barbara E. Laughon et al., “Prevalence of Enteric Pathogens in Homosexual Men With and Without Acquired Immunodeficiency Syndrome,” *Gastroenterology*, 94:984–992 (Apr. 1988).

Jill Nord et al., “Treatment with Bovine Hyperimmune Colostrum of Cryptosporidial Diarrhea in AIDS Patients,” *AIDS*, 4:581–584 (1990).

Roger J. Panciera, D.V.M., M.S., Ph.D., “Cryptosporidiosis,” *Current Veterinary Therapy*, 779–780, (1981).

Carolyn Petersen, “Cryptosporidiosis in Patients Infected with the Human Immunodeficiency Virus,” *Clinical Infectious Diseases*, 15:903–909 (Dec. 1992).

Oblack et al. “Active Immunization of Mice Against Muscle Damage Mediated by *Candida Albicans*:” *J. Med Microbiol.*, 12(4): 503–506 (1979).

James J. Plorde, “Cryptosporidiosis,” *Harrison's Principles of Internal Medicine*, 1:803–805, (Twelfth Edition, 1991).

Rosemary Soave et al., “Cryptosporidium and Other Protozoa Including Isospora, Sarcocystis, *Balantidium Coli*, and Blastocystis,” *Principles and Practices of Infectious Diseases*, 2122–2130 (Third Edition, 1990).

Saul Tzipori et al., “Chronic Cryptosporidial Diarrhoea and Hyperimmune Cow Colostrum,” *The Lancet*, 344–345 (Aug. 8, 1987).

Beth L. P. Ungar et al., “Cessation of Cryptosporidium–Associated Diarrhea in an Acquired Immunodeficiency Syndrome Patient After Treatment With Hyperimmune Bovine Colostrum,” *Gastroenterology*, 98:486–489 (Feb. 1990).

Ashman, R. B. et al, Microbiol. Review, Dec. 1995, vol. 59(4), pp. 646–672.

Segal, E, Crit. Review, Microbiol., 1987, vol. 14(3), pp. 229–271.

Harp, JA et al, J. Parasitat, vol. 81(1) pp. 54–57, 1995.

Williams, DL et al, Int. J. Immunopharmac., vol. (4), pp. 403–410, 1989.

Scaringi, L et al, J. Gen. Microbiol, England, May, vol. 134(pt. 5), pp. 1265–1274, 1988.

Yamaguchi, H. et al, Ann. N.Y., Acad. Sci., Jun. 23, 1993, vol. 685, pp. 447–457.

Cook, JA et al, Surv. Immunol. Res., vol. 2, pp. 243–245 1983.

Cook, JA et al, Int. J. Immunopharm, vol. 4(4), p. 270, #68, 1982.

(List continued on next page.)

*Primary Examiner*—James C. Housel
*Assistant Examiner*—Ginny Allen Portner
*Attorney, Agent, or Firm*—Merchant, Gould, Smith, Edell, Welter & Schmidt, P.A.

[57] ABSTRACT

The present invention provides a vaccine composition for enhancing the immune response of a mammal against a selected antigen. The vaccine composition of the invention comprises a combination of the selected antigen and a Candida spp. antigen. Selected antigens include, for example, a bacteria, yeast, rickettsia, protozoa, virus, parasite or components thereof. The composition may also contain adjuvants known in the art. A preferred vaccine composition for immunization against the selected antigen *Cryptosporidium parvum* is disclosed. The invention also provides a method for enhancing the immune response of a mammal against a selected antigen utilizing the vaccine compositions of the invention.

6 Claims, No Drawings

OTHER PUBLICATIONS

Cook, JA et al., J. of the Reticuloendothelial Society vol. 27(6), Jun. 1980.

Holbrook, TW et al, Am. J. Trop. Med. Hyg., vol. 32(1), pp. 51–53, 1983.

Holbrook, TW et al, Infect. & Immun., vol. 32(2) pp. 542–546, May 1981.

Jareckiv, Black, JC et al, Ann. Clin. Lab. Sci, vol. 18(1), pp. 72–77, 1988.

Maheshwari, R et al, Indian J. of Med. Res., Sect. A, Infectious disease, vol. 89, Nov., pp. 396–403, 1989.

Vazquez, N et al, J. Med & Vet. Mycology, vol. 33, #6, pp. 385–393, 1995.

Obaid, KA et al, Int. J. Immunpharm, vol. 11(3), pp. 229–235, 1989.

Cutler, J. E. et al., Infect. Immun., vol. 38(3), Dec. 1982, pp. 1102–1108.

Harp, J.A. et al, J. Parasitol, vol. 81(1), 1995, pp. 54–57.

Mencacci, A. et al, Infect. Immun., Dec. 1994, vol. 62(12) pp. 5353–5360.

Carrow, E.W. et al, Infect Immun, Jul. 1985, vol. 49(1), pp. 172–181.

PHARMACEUTICAL COMPOSITION COMPRISING *CRYPTOSPORIDIUM* PARVUM OOCYSTS ANTIGEN AND WHOLE CELL CANDIDA SPECIES ANTIGEN

BACKGROUND

Cryptosporidium spp. was once thought to be a commensal organism. However, in 1955 the organism was associated with turkey enteritis. Florence G. Crawford, "Human Cryptosporidiosis," *CRC Critical Reviews and Microbiol.,* 16(2) :113–159, 113 (1988). The organism was later found to be a bovine pathogen in 1971 and a human pathogen in 1976. Id. Cryptosporidium spp. is now recognized as an important enteric protozoan pathogen, most commonly identified in cases of acute, self-limiting diarrheal diseases in poultry and mammals. Edward N. Janoff et al., "Cryptosporidium Species, a Protean Protozoan," *J. Clin. Microbiol.* 25(6):967–975, 970 (June 1987). The specie which causes disease in humans is believed to be *C. parvum.* Id. at 113.

In cattle, Cryptosporidium is most commonly seen in calves less than three weeks old. "Cryptosporidiosis," in *Current Veterinary Therapy: Food Animal Practice,* 779, (Jimmy L. Howard ed. 1990). The disease is accompanied by anorexia, dehydration, weight loss, debility and occasionally death. Id.

Although the precise prevalence of Cryptosporidium in humans is unknown, it is recognized worldwide as a common cause of enteritis. Rosemary Soave et al., "Cryptosporidium and Other Protozoa Including Isospora, Sarcocystis, *Balantidium coli* and Blastocystis," in *Principles and Practice of Infectious Diseases* 235, (Gerald L. Mandel et al., eds., 1990). The organism is commonly found in immunocompetent patients showing clinical symptoms of diarrhea. Janoff at 967. Symptoms in humans include diarrhea, abdominal pain, cramping, vomiting, anorexia, malaise and weight loss and may include death in young children and aged adults. Id. at 971. The pathogenesis of human Cryptosporidium is not completely known. Crawford at 145; Janoff at 970.

The Cryptosporidium organism is also found in immunocompromised individuals. Today, many cases of Cryptosporidium in immunocompromised individuals are in persons suffering from acquired immunodeficiency syndrome (AIDS). In one study, the most common pathogen associated with diarrhea in AIDS patients was Cryptosporidium. Barbara E. Laughon et al., "Prevalence of Enteric Pathogens in Homosexual Men With and Without Acquired Immunodeficiency Syndrome," *Gastroenterology* 94(4):984–992, 984 (April 1988). Moreover, unlike the symptoms seen in immunocompetent patients, the syndrome in immunocompromised individuals may be of greater severity and may persist for many months causing anorexia, abdominal pain, weight loss, vomiting, diarrhea, malaise, low-grade fever, and even death due to dehydration and cachexia. Janoff at 971. In addition, occasional coughing and progressive pulmonary disease are seen. Id. at 971.

Therefore, as seen in immunocompromised individuals, Cryptosporidium is not necessarily self-limiting. Id. In fact, CDC sources have reported that cumulative case fatality rates through April 1986 were significantly higher in AIDS patients affected by Cryptosporidium. Crawford at 132. Moreover, it is believed that AIDS patients who recover from clinical cryptosporidiosis still harbor low levels of Cryptosporidium oocysts. Id.

In humans, treatment of Cryptosporidium using single and multiple-drug regimens has, at best, met with limited success. Janoff at 972; Crawford at 147; K. W. Angus, "Cryptosporidiosis and AIDS," *Bailliére's Clinical Gastroenterology* 4(2):425–441, 435 (June 1990). And, while immunoprophylaxis has been suggested, a Cryptosporidium vaccine capable of producing immune stimulation has not been described. Id. at 436–37.

The use of adjuvants to enhance in vitro immune stimulation against various organisms is well known. Adjuvants known in the art include, for example, alum, aluminum hydroxide, aluminum phosphate and water-in-oil emulsions. In addition, prior art adjuvants may include components of microorganisms as immuno-stimulants, for example, Freund's-complete-adjuvant is a water-in-oil adjuvant which also contains dead Mycobacteria. Other species of bacteria are also known to enhance the immune response of a human or animal, for example, Nocardia, Bordetella and *Corynebacterium parvum.*

The use of Candida spp. antigens to stimulate specific immunity to the Candida organism is known in the art. However, the use of Candida antigens as an adjuvant material to enhance the in vitro immune response to antigens other than Candida has not previously been described.

SUMMARY OF THE INVENTION

The herein disclosed invention provides a vaccine composition for enhancing the immune response of a mammal against a selected antigen. Specifically, the composition is composed of a selected antigen and a Candida spp. antigen. According to the invention, a selected antigen may be a bacteria, yeast, rickettsia, protozoa, virus, parasite or components thereof. In a preferred embodiment, the selected antigen is *Cryptosporidium parvum* in combination with a *Candida albicans* antigen. The composition may additionally contain an adjuvant known in the art.

The invention further provides a method for enhancing the immune response of a mammal against a selected antigen by administering a vaccine composition containing a selected antigen and a Candida spp. antigen. The method provides for administration of a vaccine composition of the invention through oral, subcutaneous, intramuscular, intradermal, intramammary, intravenous or other administration methods known in the art.

DETAILED DESCRIPTION OF THE INVENTION

The present invention provides a vaccine composition and a method for manufacturing a vaccine composition which enhances a mammal's immune response against a selected antigen. This includes antigens which typically do not stimulate a strong immune response due to poor antigen recognition by a human or animal's immune system. The invention also provides a method for enhancing the immune response of a mammal against a selected antigen by administering the vaccine composition of the invention to a mammal through methods commonly used in the art.

It will be noted that at several places throughout the present Specification, guidance is provided through lists of examples. In each instance, the recited lists serve only as representative groups. It is not meant, however, that the lists are exclusive.

According to the invention, the herein disclosed vaccine composition is prepared by combining a selected antigen and a Candida spp. antigen. Although the inventors do not wish to be limited to a single mechanism, it is believed that when administered to a mammal, a Candida spp. antigen acts to enhance the immune response to a selected antigen which is combined with the Candida spp. antigen. The discovery of the unexpected ability of Candida spp. antigen to enhance a mammal's immune response, including the response against poorly recognized antigens, is significant to the present invention. The immune enhancing affect of a Candida spp. antigen is seen in both the primary and secondary (anamnestic) immune response.

As used herein, the term "antigen" means a substance or entity that is structurally or functionally capable of inducing an immune response in a mammal. This includes antigens which typically produce only a very poor immune response. According to the invention, an "antigen" includes, but is not limited to, inactivated whole microorganisms, attenuated whole microorganisms, whole viral particles, antigenic microorganism/viral components or fragments, chemically or physically modified antigens, recombinant antigens, and other antigens or combinations thereof known and used in the art. The phrase "enhanced immune response" means an increase in either or both of the humoral or cellular immune response of a mammal.

In a preferred embodiment of the vaccine composition, the selected antigen which is combined with the Candida spp. antigen is derived from Cryptosporidium spp. Fundamental to a vaccine composition of the present invention is the unexpected discovery that a Candida spp. antigen combined with a selected antigen enhances the mammalian immune response against the selected antigen in the absence of other adjuvants. However, the invention also provides for combining the selected antigen and a Candida spp. antigen with one or more adjuvants known in the art to further enhance the immune response. Nonetheless, the immune enhancing effect of a Candida spp. is independent of the absence or presence of additional adjuvants.

As used herein, a Candida spp. antigen may be a whole Candida spp. organism in any of its forms (e.g., hyphal form, budding form, etc.), inactivated whole organism, fragments or components isolated from the whole organism or specific Candida spp. antigens produced through genetic engineering methods known in the art. Preferably, the Candida spp. antigen of the invention is prepared by inactivation of a live Candida spp. organism. Methods of inactivation useful according to the invention, include, for example, formaldehyde inactivation, heat treatment, hypochlorite inactivation, irradiation and other methods known in the art. Also, if the vaccine composition is combined with one or more adjuvants known in the art, the inventors recognize that many of the known adjuvants may serve to inactivate the Candida spp. organism without the Candida spp. first being inactivated by the above recited methods.

A selected antigen against which immunity is desired may be prepared by methods commonly used in the art. As used herein, a selected antigen may be a whole organism in any of its life cycle stages, inactivated whole organism, fragments or components isolated from the whole organism, specific antigens genetically engineered through methods known in the art or other antigens as defined earlier in this disclosure. In addition, the selected antigen may be derived from either or both a mature whole organism or sporozoites (oocysts). Preferred selected antigens of the invention include, for example, antigens from bacteria, yeast, protozoa, viruses, rickettsia, and parasites such as helminths. A particularly preferred selected antigen is derived from the protozoan, *Cryptosporidium parvum.*

The vaccine composition of the invention is prepared by combining the Candida spp. antigen with the selected antigen. When using an inactivated whole cell Candida spp. antigen, the number of cells in a single mammalian dose of vaccine is about $2\times10^3$ to $2\times10^{11}$, preferably $2\times10^6$ to $2\times10^9$. The amount of a selected antigen to be administered to a mammal in a single dose of the vaccine composition will vary with the selected antigen and can be readily quantitated by one of skill in the art. When the selected antigen is Cryptosporidium spp., a single mammalian dose of a vaccine composition may contain $2\times10^4$ to $2\times10^{12}$ oocysts, preferably $2\times10^5$ to $2\times10^9$ oocysts.

Although it is not deemed necessary, a vaccine composition of the invention containing a selected antigen and Candida spp. antigen may be further combined with a pharmaceutically acceptable carrier. Pharmaceutically acceptable carriers useful according to the invention include physiological saline, ringers, lactated ringers, phosphate buffered saline and other carriers known in the art.

Additionally, a vaccine composition of the invention may include a selected antigen, Candida spp. antigen and one or more adjuvants selected from adjuvants known in the art. When an adjuvant is mixed with the Cryptosporidium and Candida antigen, the adjuvant is mixed with the combined antigens in a volume/volume (v/v) ratio of 3:1 to 1:5, preferably 1:1. Adjuvants known in the art which are suitable for the invention include, but are not limited to, incomplete Freund's adjuvant (IFA), Freund's complete adjuvant, saponins, Quil A, mineral oil, aluminum hydroxide, aluminum phosphate, muramyl dipeptide, block copolymers and synthetic polynucleotides.

The present invention further provides a method for enhancing the immunity of a mammal to a selected antigen by administering a vaccine composition of the invention to a mammal through methods known in the art. Such methods of administration include enteral administration and parenteral such as subcutaneous, intramuscular, intradermal, intramammary and intravenous administration.

The enhanced immunity to selected antigens provided by administering a vaccine composition of the invention was studied using animal models. Mouse inoculation studies using a selected antigen of *Cryptosporidium parvum* and a *Candida albicans* antigen, regardless of the presence or absence of additional adjuvants, provided significantly higher *C. parvum serum* immunoglobulin titers than when *C. albicans* antigen was omitted. Calf inoculation studies using a *C. parvum* antigen and a *C. albicans* antigen, regardless of the presence or absence of the additional adjuvants, also produced a significant increase in *C. parvum* serum immunoglobulin titers over titers produced in calves inoculated with the *C. parvum* antigen alone. The enhanced immune response was detectable after a primary or a secondary immunization with a composition of the invention.

The following examples describe preparation of a vaccine composition against the selected antigen *C. parvum* and the results of immunization studies performed.

EXAMPLES

EXAMPLE 1

Preparation of *Cryptosporidium parvum* and *Candida albicans* vaccine compositions

*Cryptosporidium parvum* vaccine compositions were prepared with multiple concentrations of *C. parvum* antigen and multiple concentrations of *C. albicans* antigen. Vaccine compositions containing *C. parvum* antigens, *C. albicans* antigen and various additional adjuvants were also prepared and tested.

Vaccine compositions were prepared to provide $8\times10^6$ Cryptosporidium oocysts and $2\times10^7$ Candida cells per dose of mouse vaccine and $3\times10^8$ Cryptosporidium oocysts and $2\times10^7$ Candida cells per dose of calf vaccine.

The vaccine compositions were prepared by combining *C. parvum* oocysts with *C. albicans* cells in a ratio of about 1:1 to 1:10, preferably 1:3 to 1:6. The *Cryptosporidium parvum* oocysts and the *Candida albicans* cells were counted using a hemocytometer (Hausser Scientific, Horsham, Pa.). The *Cryptosporidium parvum* antigen was prepared using three cycles of freezing and thawing of *C. parvum* oocysts. The *C. albicans* antigen was prepared by adding 1% formaldehyde to *Candida albicans* cells to a final concentration of 0.37%.

The additional adjuvant used in some vaccine compositions were incomplete Freund's adjuvant (IFA) and mineral oil. Phosphate buffered saline (PBS) was used as a control. The *C. parvum* and *C. albicans* preparations as described above were combined with an adjuvant in a 1:1 v/v ratio. Vaccine compositions containing mineral oil were prepared by simply mixing the mineral oil with the Cryptosproidium and Candida antigen combination. Vaccine compositions containing IFA were emulsions prepared by mixing IFA with the Cryptosporidium and Candida antigen combination followed by sonication with a microprobe at 25 watts for 30 seconds at 100% power. PBS, mineral oil and IFA are commonly available to those skilled in the art.

Some of the various vaccine combinations prepared are shown in Table 1. The table also shows antigen quantities used per immunizing dose.

TABLE 1

| | Antigen Quantities per Immunization | | Adjuvants |
|---|---|---|---|
| | MOUSE VACCINE COMPOSITIONS | | |
| 1 | $8\times10^6$ Crypto | PBS | Incomplete Freund's Adjuvant |
| 2 | $8\times10^6$ Crypto | $2\times10^7$ Candida | Incomplete Freund's Adjuvant |
| 3 | $8\times10^6$ Crypto | PBS | Mineral Oil |
| 4 | $8\times10^6$ Crypto | $2\times10^7$ Candida | PBS |
| 5 | $8\times10^6$ Crypto | $2\times10^7$ Candida | Mineral Oil |
| | CALF VACCINE COMPOSITIONS | | |
| 1 | $3\times10^8$ Crypto | $2\times10^9$ Candida | Incomplete Freund's Adjuvant |
| 2 | $3\times10^8$ Crypto | $2\times10^9$ Candida | PBS |
| 3 | $3\times10^8$ Crypto | PBS | Incomplete Freund's Adjuvant |
| 4 | PBS | $2\times10^9$ Candida | Incomplete Freund's Adjuvant |

EXAMPLE 2

Preparation of Mouse Vaccine

To prepare a mouse vaccine composition, 5ml of $8.0\times10^7$/ml *Cryptosporidium parvum* oocysts were combined with 5.0 ml of $2\times10^8$/ml *Candida albicans* cells. If an additional adjuvant was used, 1.0 ml of the combined *C. parvum* and *C. albicans* antigens were mixed with 1.0 ml of adjuvant.

The 5.0 ml of $8.0\times10^7$/ml *C. parvum* oocysts were prepared by mixing 0.075 ml *C. parvum* oocysts with 4.925 ml PBS. The 5.0 ml $2\times10^8$/ml *C. albicans* cells were prepared by mixing 1 ml of $1\times10^9$/ml *C. albicans* cells with 4 ml PBS. The final relative concentration of the combined Cryptosporidium and Candida antigens was $4\times10^7$/ml and $1\times10^8$/ml, respectively.

If adjuvant was used, 1.0 ml of the mixed Cryptosporidium and Candida antigen was mixed with 1.0 ml of adjuvant. When mineral oil was used as an adjuvant, the adjuvant was combined with the antigens by simple mixing. When IFA was used, an emulsion was formed using a microprobe as described in Example 1. Therefore, the mouse vaccine composition contained $2\times10^7$/ml *C. parvum* oocysts and $5\times10^7$/ml *C. albicans* cells.

EXAMPLE 3

Preparation of Calf Vaccine

To prepare a calf vaccine composition, 50 ml of $6.4\times10^8$/ml *Cryptosporidium parvum* oocysts were combined with 50 ml of $4\times10^9$/ml *Candida albicans* cells. If an additional adjuvant was used, 1.0 ml of the combined *C. parvum* and *C. albicans* cells was mixed with 1.0 ml of adjuvant.

The 50 ml of $6.4\times10^8$/ml *C. parvum* oocysts/sporozoites were prepared by mixing 16 ml of $2\times10^9$/ml *C. parvum* oocysts with 34 ml PBS. The 5.0 ml of $4\times10^9$/ml *C. albicans* cells was prepared by mixing 40 ml of $5\times10^9$/ml *C. albicans* cells with 10 ml PBS. The final relative concentrations of the combined *C. parvum* and *C. albicans* antigens were $3.2\times10^8$/ml and $2\times10^9$/ml, respectively.

If adjuvant was used, 1.0 ml of the mixed Cryptosporidium and Candida antigen was mixed with 1.0 ml of adjuvant. When mineral oil was used as an adjuvant, the antigens and adjuvant were simply mixed together. When IFA was used, an emulsion was formed using a microprobe as described in Example 1. Therefore, the calf vaccine composition contained $1.6\times10^8$/ml *C. parvum* oocysts and $1\times10^9$/ml *C. albicans* cells.

EXAMPLE 4

Mouse immunization studies

Mice were immunized with vaccine compositions prepared as described in Examples 1 and 2. Balb\c mice 6–8 weeks of age were used for the immunization study. Mice were divided into immunization groups with 4 mice in each group. Vaccine was administered subcutaneously by holding each mouse behind the head in a manner to leave the skin behind and below the shoulder blades as loose as possible. A total of 400 $\mu$l per mouse was administered using a 22 gauge needle. Hence, each 400 $\mu$l dose contained $8\times10^6$/ml *C. parvum* oocysts and $2\times10^7$/ml *C. albicans* cells. A total of 3 immunization doses were given at approximately 2-week intervals.

Tail bleeds were performed at approximately 6½ weeks to obtain serum samples for testing antibody response. The tip (about 1 mm) of the tail was cut off using a sharp razor blade. Approximately 50 $\mu$l of blood was collected into 1.5 ml microcentrifuge tubes and allowed to coagulate overnight at 4° C. Samples were then spun in a microcentrifuge for 3 minutes at approximately 14,000xg to separate the serum from the clot. ELISA assays were used to determine serum titers of the mice to both *C. parvum* and *C. albicans* antigens.

Pooled serum samples were also tested. At about 7 weeks the mice were bled out to collect a larger volume of serum. The mice were first anesthetized with a mixture of tribromoethanol and tert-amyl alcohol and ocular bleeds were performed. The blood was collected into microcentrifuge tubes. Serum was separated in the same manner as the tail bleeds described above. Six serum pools representing the six immunization groups were then made by combining 200 $\mu$l of serum from the 4 individual mice of each group. The pooled serum from the 6 immunization groups were titered in ELISA assays to both *C. parvum* and *C. albicans* antigens. As shown below, titers from the serum pools were similar to the mathematical averages of the individual serum samples from each immunization group. *C. albicans* titers over non-immune titers was also assayed on pooled samples and were determined to be unaffected by the presence of *C. parvum* antigens (i.e., adjuvant effect was one-way).

TABLE 2

MICE IMMUNIZATION

| Immunization Group | | | | Cryptosporidium parvum Titers (Titers Over Non-Immune Serum) | | | | |
|---|---|---|---|---|---|---|---|---|
| | | | | Mouse Number | | | | |
| | Cryp-to | Can-dida | Adjuvant | 1 | 2 | 3 | 4 | POOL |
| 1 | X | — | IFA | 800 | 400 | 400 | 400 | 800 |
| 2 | X | X | IFA | 12800 | 800 | 25600 | 1600 | 12800 |
| 3 | X | — | Mineral Oil | 400 | 200 | 200 | 400 | 400 |
| 4 | X | X | — | 1600 | 800 | 800 | 800 | 800 |
| 5 | X | X | Mineral Oil | 1600 | 400 | 800 | 3200 | 1600 |

EXAMPLE 5

Calf Immunization Studies

Calves were immunized with vaccine compositions prepared as described in Examples 1 and 3.

Four to six month old Holstein steer calves were used for this immunization study. All calves were healthy and, prior to the study, were treated with vitamin E-selenium, vitamin B complex and ivermectin. Calves were individually identified with 2 means of permanent identification and boostered with a killed vaccine preparation against IBR, $PI_3$, BRSV and BVD (Elite 4, Bio-Ceutic Laboratories, St. Joseph, Mo.). All calves were fed free choice hay supplemented with a balanced grain ration containing a coccidiostat (decoquinata).

The calves were randomly assigned to treatment groups of four (4) to five (5) calves per group. The calves were allowed to commingle during the study.

Each vaccine composition was administered intramuscularly. A total of 2 ml of the vaccine composition of Examples 1 and 3 was administered 4 times at 2-week intervals. Hence, each 2 ml dose contained $3.2\times10^8$/ml *C. parvum* oocysts and $2\times10^9$/ml *C. albicans* cells.

The injection site of each inoculation was observed at the time of inoculation, at 24 hours post-inoculation and at weekly intervals for the duration of the study. No adverse systemic reactions were noted. Induction of a significant immune response was frequently associated with an unacceptable localized inflammatory response when an additional adjuvant was used.

Venous blood samples were taken at the time of each immunization and up to four weeks after the final injection to obtain serum samples for assessing antibody response. Approximately 20 ml of blood was collected into sterile tubes and allowed to coagulate overnight at 4° C. Samples were then spun in a centrifuge for 3 minutes at approximately 14,000×g to separate the serum from the clot. ELISA assays were used to determine serum titers of the calves to both *C. parvum* and *C. albicans* antigens.

TABLE 3

CALF IMMUNIZATION

| Immunization Group | | | | Cryptosporidium Titers (Calf Titers Over Non-Immune Serum) | | | | | |
|---|---|---|---|---|---|---|---|---|---|
| | | | | Calf Number | | | | | |
| | Crypto | Candida | Other | 1 | 2 | 3 | 4 | 5 | Average |
| 1 | X | X | IFA | 64 | 128 | 64 | 64 | 64 | 80 |
| 2 | X | X | PBS | 16 | 128 | 32 | 128 | — | 76 |
| 3 | X | — | PBS | 32 | 64 | 32 | 32 | — | 40 |

The potentiation of the immune response stimulated by a composition of the invention was evident even after primary immunization. Preimmunization titers were calculated relative to a non-immune control pooled serum standard.

TABLE 4

| Calf Number | Preimmunization Titer | Post Primary Immunization Titer | Increase |
|---|---|---|---|
| VACCINE COMPOSITION USED: CRYPTO + CANDIDA + IFA | | | |
| 101 | 0.75 | 8 | 10.6× |
| 108 | 0.75 | 16 | 21.3× |
| 115 | 1.5 | 4 | 2.7× |
| 122 | 0.75 | 8 | 10.6× |
| 129 | 0.5 | 8 | 16× |
| VACCINE COMPOSITION USED: CRYPTO + IFA | | | |
| 110 | 2 | 2 | — |
| 117 | 0.25 | 1 | 4× |
| 124 | 0.5 | 1 | 2× |
| 005 | 2 | 4 | 2× |

All publications in the specification are indicative of the level of ordinary skill in the art to which this invention pertains and are incorporated herein by reference.

It will be apparent to one of ordinary skill in the art that many changes and modifications can be made in the invention without departing from the spirit or scope of the appended claims.

What is claimed is:

1. A pharmaceutical composition comprising a whole cell Candida species antigen and an inactivated *Cryptosporidium parvum* oocyst.

2. The composition according to claim 1, further comprising at least one additional adjuvant.

3. The composition according to claim 2, wherein the additional adjuvant is incomplete Freund's adjuvant.

4. The composition according to claim 1, wherein the whole cell Candida antigen is inactivated whole cell *Candida albicans*.

5. A pharmaceutical composition for enhancing the immune response of a mammal against *Cryptosporidium parvum* comprising a *Cryptosporidium parvum* oocyst antigen and a whole cell Candida species antigen.

6. The composition according to claim 5, wherein the whole cell Candida antigen is inactivated whole cell *Candida albicans*.

* * * * *